(12) United States Patent
Hsu et al.

(10) Patent No.: US 8,845,869 B2
(45) Date of Patent: Sep. 30, 2014

(54) ELECTROCHEMICAL SENSOR STRIP

(75) Inventors: Cheng-Teng Hsu, Taichung (TW); Hung-Chan Hsiao, Taichung (TW)

(73) Assignee: Bionime Corporation, Taichung (TW)

( * ) Notice: Subject to any disclaimer, the term of this patent is extended or adjusted under 35 U.S.C. 154(b) by 211 days.

(21) Appl. No.: 13/238,354

(22) Filed: Sep. 21, 2011

(65) Prior Publication Data

US 2012/0073966 A1   Mar. 29, 2012

(30) Foreign Application Priority Data

Sep. 23, 2010   (TW) ............................... 99132170 A (51) Int. Cl.
*G01N 27/327* (2006.01)
(52) U.S. Cl.
CPC .................................. *G01N 27/3272* (2013.01)
USPC .................... 204/403.01; 204/403.06; 435/25
(58) Field of Classification Search
USPC ............. 204/403.01–403.15; 205/777.5, 778, 205/792; 600/345–348; 435/4–40.52; 422/68.1–98; 436/62–71, 500–548
See application file for complete search history.

(56) References Cited

U.S. PATENT DOCUMENTS

| | | | |
|---|---|---|---|
| 5,139,685 A | | 8/1992 | de Castro et al. |
| 5,628,890 A | | 5/1997 | Carter et al. |
| 5,652,050 A | * | 7/1997 | Pall et al. ...................... 442/394 |
| 6,054,039 A | | 4/2000 | Shieh |
| 6,319,719 B1 | | 11/2001 | Bhullar et al. |
| 6,966,977 B2 | | 11/2005 | Hasegawa et al. |
| 2004/0096928 A1 | * | 5/2004 | Hasegawa et al. .............. 435/25 |
| 2010/0243442 A1 | | 9/2010 | Huang et al. |

FOREIGN PATENT DOCUMENTS

| | | |
|---|---|---|
| CN | 1201147 C | 5/2005 |
| CN | 1675539 A | 9/2005 |
| CN | 101520428 A | 9/2009 |
| CN | 101561411 A | 10/2009 |
| TW | 416005 B | 12/2000 |
| TW | M252016 U | 12/2004 |

OTHER PUBLICATIONS

Hsu, C.-T., et al. "Fabrication of a glucose biosensor based on inserted barrel plating gold electrodes" Analytical Chemistry, vol. 81, No. 1, Jan. 1, 2009, p. 515-518.*
Hsu, C.-T., et al. "Assessing the quality of Bionime self-monitoring blood glucose system Rightest GM110: A critical evaluation of interference and ambient circumstances" Clinica Chimica Acta, vol. 402, No. 1-2, Apr. 2009, p. 119-123.*
Hsu, C.-T., et al. "Superior long-term stability of a glucose biosensor based on inserted barrel plating gold electrodes" Biosensors and Bioelectronics, vol. 25, No. 2, Oct. 2009, p. 383-387.*
Machine translation of Lianghong—CN 101561411, A.*
Search Report dated Apr. 11, 2013 of corresponding application No. CN 201010501028.5 with English Translation.

* cited by examiner

*Primary Examiner* — J. Christopher Ball
(74) *Attorney, Agent, or Firm* — Pepper Hamilton LLP (57) ABSTRACT

An electrochemical sensor strip includes an electrode support and a cover plate, which cooperatively defines a sample receiving space, an opening, and a sample passage. The electrode support has a downstream recessed region defining the sample receiving space and formed with a plurality of through holes. Electrodes are disposed respectively in the through holes. At least one of the electrodes has a lowered top surface that is lowered relative to a surface of the downstream recessed region to define a shallow space. A filter extends into the sample receiving space from the opening and through the sample passage and covers a portion of a reaction reagent layer. The reaction reagent layer extends into the shallow space. The filter extends above the shallow space and the electrode.

17 Claims, 9 Drawing Sheets

ELECTROCHEMICAL SENSOR STRIP

CROSS REFERENCE TO RELATED APPLICATION

This application claims priority of Taiwanese Application No. 99132170 filed on Sep. 23, 2010.

BACKGROUND OF THE INVENTION

1. Field of the Invention

The invention relates to a sensor strip, and more particularly to an electrochemical sensor strip.

2. Description of the Related Art

Electrochemical sensor strips have been widely used in analysis of various kinds of fluids. Generally, such sensor strips include a container for receiving fluid to be tested, a reaction reagent layer fixed in the container for reacting electrochemically with a target analyte in the fluid, and an electrode system mounted in the container. A reaction between the reagent and the analyte will generate an output signal involving an electric characteristic parameter, and the concentration of the analyte in the fluid can be determined based on the electric characteristic parameter. The electrode system includes a counter electrode, a working electrode, a reference electrode and a detecting electrode. By varying the reaction reagent used in the container, different kinds of electrochemical sensors may be fabricated for detection of various analytes, such as, blood sugar, urine acidity, cholesterol concentration in blood, and heavy metals, pesticides, and other toxic components in polluted water.

To ensure accurate detection results of an electrochemical sensor, interfering substances that may interfere with the detection result are usually removed from the fluid to be analyzed beforehand. Taking whole blood as an example, since red blood cells can affect the detected result of the sensor, a membrane filter is disposed between an opening of the container and the reaction reagent layer to filter and separate the red cell bloods from blood plasmas in the whole blood. U.S. Pat. No. 5,139,685 discloses a glass fiber membrane filter for separating blood cells and blood plasmas without the need of centrifugal separation. However, when the amount of the blood under test is small, the amount of the filtrate produced by the filter can be considerably small, and a certain pressure has to be applied to completely filter out the blood cells in the whole blood. Furthermore, homolysis is likely to occur when subjected to pressure, thereby resulting in an inaccurate result. Moreover, the blood plasmas absorbed by the filter tends to slow down the flow rate of the blood plasmas, and hence a longer time is needed to obtain the sensing result.

Figure 1:
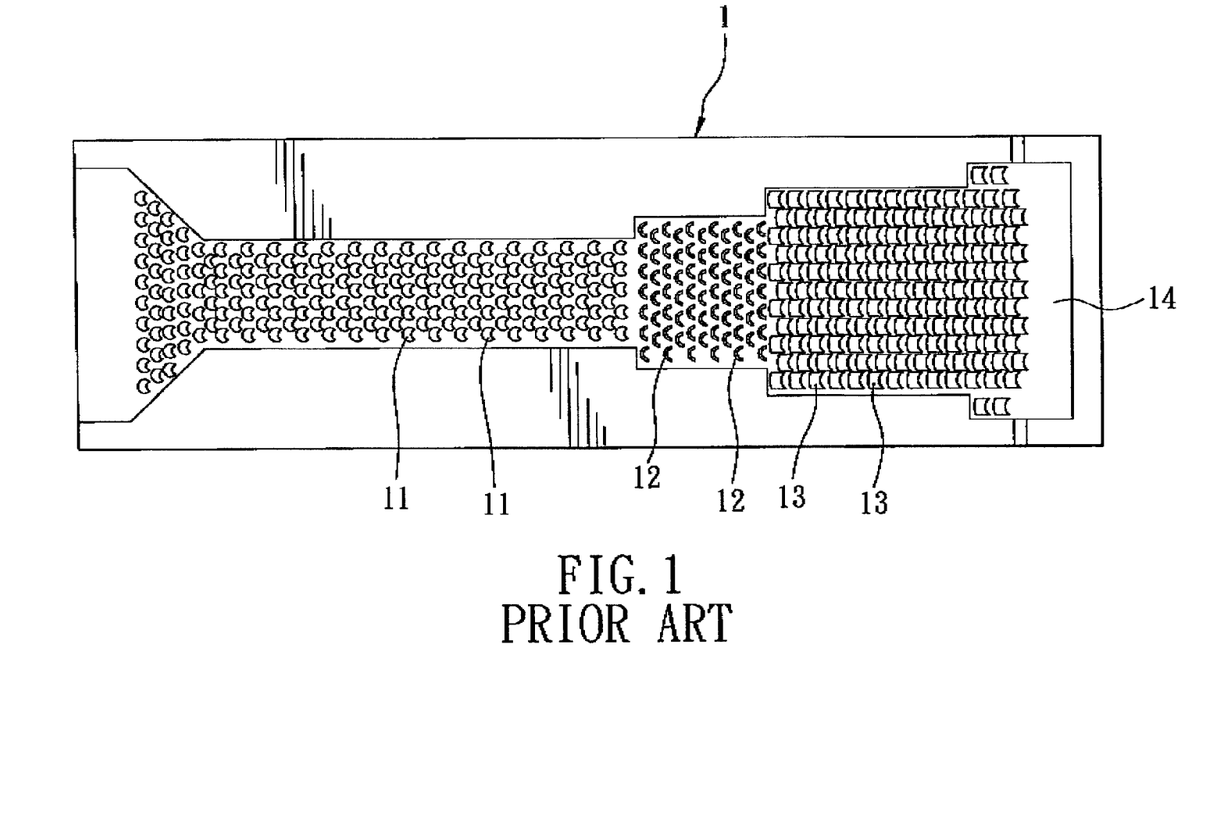
FIG. 1 is a plan view illustrating a plurality of obstructions provided in an electrochemical sensor disclosed in U.S. Pat. No. 6,319,719.

Referring to FIG. 1, an electrochemical sensor 1 disclosed in U.S. Pat. No. 6,319,719 is provided with a plurality of spaced apart crescent-shaped first, second and third obstructions 11, 12 and 13 disposed in a fluid passage for retarding and removing red blood cells from a whole blood and for permitting blood plasma to quickly flaw through the obstructions 11, 12, 13 and to move to a reaction reagent layer 14. However, this sort of design requires a larger space for providing the obstructions 11, 12, 13 in an amount sufficient for separation resulting in the need of a relatively large amount of blood to obtain a detection result smoothly. Moreover, because an etching process is needed to provide the obstructions 11, 12, 13 with particular size, shape and spacing, fabrication of such a sensor requires a relatively long production time and a relatively high production cost.

U.S. Pat. No. 6,966,977 discloses an electrochemical sensor strip that includes a filter to filter a fluid to be analyzed and to guide blood plasmas to move to a reaction reagent layer and an electrode system. The filter has, at an upstream side thereof, a cross-sectional area larger than a cross-sectional area of an opening of a sample solution supply pathway, and also larger than a cross-sectional area at a downstream side thereof. The sample solution supply pathway has a cross-sectional area equal to or smaller than the cross-sectional area of the opening of the sample solution supply pathway. However, the electrochemical sensor strip has the following disadvantages:

1. The downstream side of the filter cannot extend through the open end of the sample solution supply pathway, otherwise the filter will contact the electrode system and cause an adverse affect to detection results. Moreover, although variation of the cross section of the filter enables the blood plasmas to quickly reach a front end of the filter, a relatively long time is needed to have the fluid accumulated to an amount sufficient for detection.

2. Since the sample solution supply pathway is sized to match with the electrode system and the reaction reagent layer, the size thereof cannot be varied easily. In order for the cross section of the upstream side to be larger than that of the downstream side, the filter must have a wide or thick size. An increase in size of the filter results in the need of an increased fluid amount and an increased sensing time.

U.S. Pat. No. 5,628,890 discloses an electrochemical sensor strip in which filter layers and electrodes are arranged in a stack, and all electrodes (three electrodes) are covered by the filter layers. The structure disclosed therein can reduce the distance between the electrode unit and the point where the fluid is dropped and thereby increase the speed of obtaining the sensing result. However, the number of the filter layers has to be increased, and an electric isolation layer made of a hydrophobic material is additionally needed. The resulting multi-layered structure has to be made up of a number of component parts and requires a micropump or a pressurizing force for driving the fluid.

SUMMARY OF THE INVENTION

An object of the present invention is to provide an electrochemical sensor strip that improves the accuracy of results and increases the speed of detection, that is easy to manufacture, and that has an improved quantitative detection performance for a target analyte.

Accordingly, the present invention provides an electrochemical sensor strip which comprises a housing, an electrode unit, a reaction reagent layer and a filter. The housing includes an electrode support and a cover plate, which cooperatively define a sample receiving space, an opening, and a sample passage connected to the opening and the sample receiving space. The electrode support has an inner surface confronting the cover plate, an outer surface opposite to the inner surface, an upstream recessed region formed in the inner surface to define the sample passage, and a downstream recessed region formed in the inner surface to define the sample receiving space, and a plurality of through holes extending through the inner and outer surfaces within the downstream recessed region. The electrode unit includes a plurality of electrodes disposed respectively in the through holes, at least one of the electrodes having a lowered top surface that is lowered relative to the inner surface to define a shallow space within a respective one of the through holes. The reaction reagent layer is disposed in the sample receiving space in contact with the electrodes and extending into the shallow space. The filter is made of a material having a porous structure and extends into the sample receiving space from the opening and through the sample passage. The filter covers a portion of the reaction reagent layer and extends above the shallow space and the lower top surface.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Before the present invention is described in greater detail with reference to the accompanying preferred embodiments, it should be noted herein that like elements are denoted by the same reference numerals throughout the disclosure.

Figure 2:
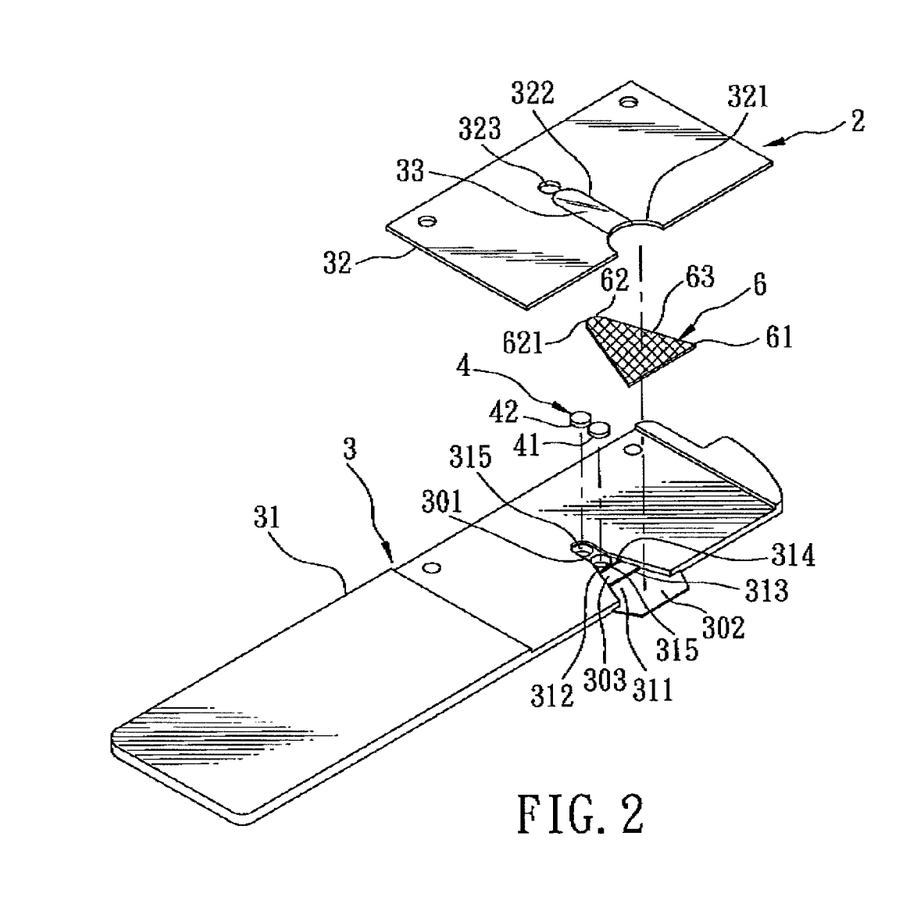
FIG. 2 is an exploded perspective view illustrating a preferred embodiment of an electrochemical sensor strip according to the present invention.
Figure 3:
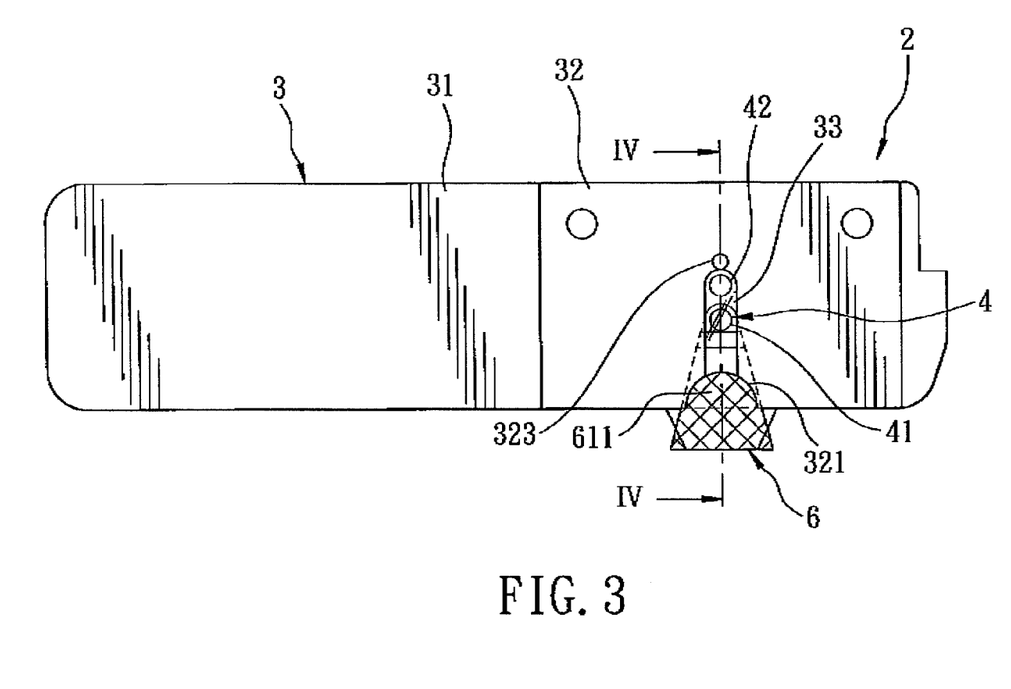
FIG. 3 is a plan view of the first preferred embodiment.
Figure 4:
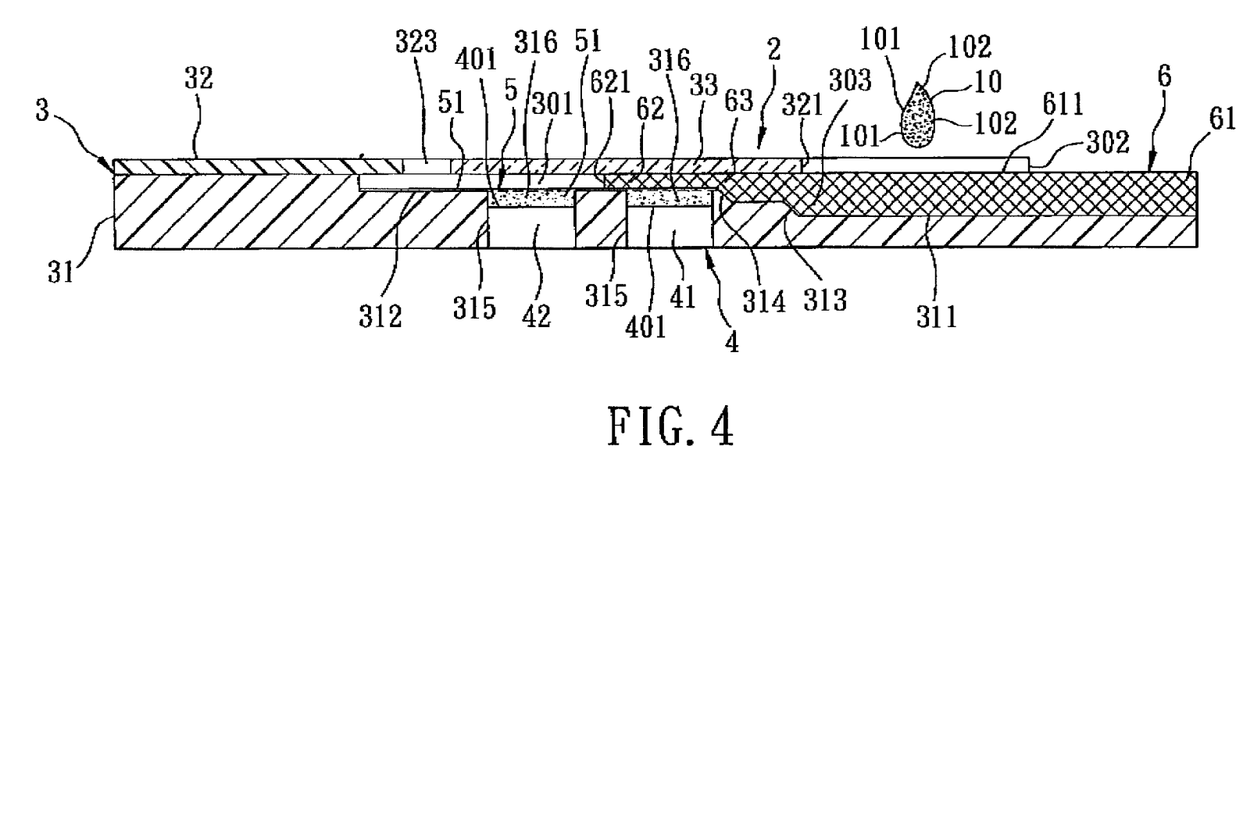
FIG. 4 is a sectional view taken along line IV-IV in FIG. 3.

Referring to FIGS. 2 to 4, a preferred embodiment of an electrochemical sensor strip according to this invention is shown at 2, and is usable for sensing a target analyte 101 in fluid 10 to be analyzed. The electrochemical sensor strip 2 includes a housing 3, an electrode unit 4 mounted in the housing 3, a reaction reagent layer 5 mounted in the housing 3 and contacting the electrode unit 4, and a filter 6 mounted in the housing 3 and covering a portion of the electrode unit 4 and a portion of the reaction reagent layer 5. In this embodiment, the fluid 10 is a whole blood, the target analyte 101 is blood sugar, and blood cells 102 constitute an interfering matter in the whole blood. However, what is disclosed herein should not be imposed as a restriction of the type of the electrochemical sensor strip 2. By varying the reagent composition used in the reaction reagent layer 5, the electrochemical sensor 2 may be used to detect other analytes, such as blood sugar, urine acidity, cholesterols, heavy metal, pesticide, etc.

The housing 3 includes an electrode support 31 and a cover plate 32, which cooperatively define a sample receiving space 301, an opening 302, and a sample passage 303 connected to the opening 302 and the sample receiving space 301.

The electrode support 31 has an inner surface confronting the cover plate 32, an outer surface opposite to the inner surface, an upstream recessed region 311 formed in the inner surface to define the sample passage 303, a downstream recessed region 312 formed in the inner surface to define the sample receiving space 301, and a plurality of spaced apart through holes 315 extending through the inner and outer surfaces within the downstream recessed region 312. The upstream recessed region 311 has a stepped surface that ascends from the opening 302 to the downstream recessed region 312. The filter 6 extends along the stepped surface and is clamped between the electrode support 31 and the cover plate 32. In this embodiment, the upstream recessed region 311 has a first stepped portion 313 proximate to the opening 302, and a second stepped portion 314 proximate to the downstream recessed region 312. The height of the second stepped portion 314 is higher than that of the first stepped portion 313. Each of the first and second stepped portion 313, 314 forms a corner with an obtuse angle of larger than 90 degrees. The number of the stepped portions can be varied according to an actual demand.

The cover plate 32 has a peripheral edge formed with an arcuated notch 321 that is proximate to the opening 302 and that is indented in a direction toward the sample receiving space 301 so as to expose a portion of the filter 6. The cover plate 32 further has a viewing hole 322 extending from the arcuated notch 321 to the sample receiving space 301 and along the sample passage 303, and a plurality of vent holes 323 formed above the downstream recessed region 312. The vent holes 315 facilitate the capillary flow of the fluid 10 to the sample receiving space 301 through the filter 6 and along the sample passage 303.

Preferably, the housing 3 further includes a viewing window 33 to cover the viewing hole 322 and to permit a user to observe the fluid 10 flowing through the filter 6 disposed in the sample passage 303.

The electrode unit 4 includes a plurality of electrodes disposed respectively in the through holes 315. At least one of the electrodes has a lowered top surface 401 that is lowered relative to the inner surface of the electrode support 31 within the downstream recessed region 312.

In this embodiment, the electrode support 31 is formed with a pair of the through holes 315, and the electrode unit 4 includes a first electrode 41 and a working electrode 42 press fitted in the through holes 315, respectively. Both of the first and working electrodes 41, 42 have the lowered top surfaces 401. The first electrode 41 may be a counter electrode, a reference electrode, and a combination thereof. In this embodiment, the first electrode 41 is a dual counter and reference electrode. The first electrode 41 is proximate to the upstream recessed region 311, and the working electrode 42 is distal from the upstream recessed region 311. But, in practice, the positions of the first electrode 41 and the working electrode 42 may be interchanged to achieve the same function. After the first and working electrodes 41, 42 are fitted in the respective through holes 315, the lowered top surfaces 401 thereof respectively define shallow spaces 316 in the through holes 315. While two electrodes are used in this embodiment, the number of the electrodes should not be limited only thereto. The electrode unit 4 may be a tri-electrode system that includes a working electrode, a counter electrode and a reference electrode, or a multi-electrode system that includes a working electrode, a counter electrode, a reference electrode, and at least one detecting electrode. Besides, in place of the two shallow spaces 316, only one shallow space 316 may be formed by lowering the top surface of one of the first or working electrode 41, 42, which is proximate to the upstream recessed region 311.

The reaction reagent layer 5 is disposed in the sample receiving space 301 in contact with the first and working electrodes 41, 42, and includes a sensing reagent 51 for reacting with a target analyte 101. The sensing reagent 41 is applied to the inner surface in the downstream recessed region 312 and is filled in the shallow spaces 316 above the lowered top surfaces of the first and working electrodes 41, 42.

The filter 6 is made of a porous material with a pore size in a range of 0.8 μm-8 μm. The filter 6 extends into the sample receiving space 301 from the opening 302 and through the sample passage 303, and covers a portion of the reaction reagent layer 5. The filter 6 extends above a portion of the electrode unit 4. In this embodiment, the filter 6 extends above one of the two lowered top surfaces 401 of the first and working electrodes 41, 42, which is proximate to the sample passage 303. On the other hand, if only one of the first and the working electrodes 41, 42 has its top surface 401 lowered, then the filter 6 extends above the lowered top surface 401 only. If the electrode unit 4 is a tri-electrode system, the filter 6 may be arranged to extend above one or two of the three electrodes. Whether the electrode unit 4 is a bi-, tri- or multi-electrode system, the filter 6 is not allowed to cover all of the electrodes.

Preferably, the filter 6 has a wide section 61 disposed in the opening 302, a narrow section 62 disposed in the sample receiving space 301, and a middle section 63 interconnecting the wide and narrow sections 62 and tapering gradually from the wide section 61 to the narrow section 62. The wide section 61 has a sample access region 611 exposed from the arcuated notch 321 of the cover plate 32. In this embodiment, the filter 6 has a substantially triangular shape, and the narrow section 62 terminates at a tip end 621. In order to enable the filtrate containing the target analyte 101 to undergo an electrochemical reaction at a relatively fast rate, the filter 6 is arranged to extend into the sample receiving space 301 until the tip end 621 thereof extends over the reaction reagent layer 5 and above the electrode unit 4 (as shown in FIG. 4). As such, when the target analyte 101 enters the reaction reagent layer 5, it reaches a location close to the electrode unit 4 so that a quicker electrochemical response can be obtained from the electrode unit 4.

Due to the provision of the tip end 621 for the filter 6, the filtrate from the filter 6 can be collected quickly at the tip end 621 for delivery therefrom, thereby increasing the speed of obtaining the results of detection. Although the filter 6 extends above the first electrode 91, the shallow space 316 formed above the first electrode 41 can provide a substantial spacing between the filter 6 and the first electrode 41 so that the filter 6 may be prevented from contacting the first electrode 91 and from interfering or affecting accuracy of the detected result.

Because the filter 6 is provided with the tapering shape, the flowing speed of the fluid 10 at the tip end 621 will be different from the speed at the two lateral sides of the filter 6. If the speed difference is too large, air bubbles are likely to form in the fluid 10. In order to avoid such a phenomena, the tip end 621 of the narrow section 62 is rounded to have an arcuated profile.

According to the present invention, a gap between the upstream recessed region 311 and the cover plate 32 is gradually reduced in height from the opening 302 to the sample receiving space 301 so that the filter 6 will be subjected to a squeezing pressure, which increases from the opening 302 to the sample receiving space 301. Moreover, the density of the filter 6 increases from the opening 302 to the sample receiving space 301. Because the pore size of the filter 6 decreases from the opening 302 to the sample receiving space 301, the interfering matter 102 (e.g., red blood cell) will encounter a larger retarding force when flowing to the tip end 621, resulting in a quicker separation of the interfering matter 102 from the target analyte 101. Furthermore, because the upstream recessed region 311 is tapered from the opening 302 to the downstream recessed region 312 in accordance with the shape of the filter 6, the filter 6 can be received fittingly and positioned stably in the upstream recessed region 311.

While the filter 6 is made of glass fiber in this embodiment, other suitable fiber materials, such as mixed spun fibers, may be used to make the filter 6 in the present invention. In order to achieve an efficient separation and a fast flow rate of the fluid through the filter 6, the pore size of the filter 6 is arranged to be in a range of 0.8 μm-8 μm.

In use, a predetermined amount of the fluid 10 to be analyzed is dropped onto the sample access region 611 of the filter 6 exposed at the arcuated notch 321 of the cover plate 32. By virtue of the capillary action, the fluid 10 flows along the filter 6 through the sample passage 303 and toward the sample receiving space 301.

Referring back to FIGS. 2 and 3, the upstream recessed region 311 formed in the electrode support 31 is tapered from the opening 302 to the downstream recessed region 312, and the downstream recessed region 312 is tapered from the upstream recessed region 311 in a direction away from the upstream recessed region 311. By virtue of the tapered configurations of the regions 311, 312, a varying squeezing pressure can be applied to the filter 6 to vary the pore size of the filter 6.

Figure 6:
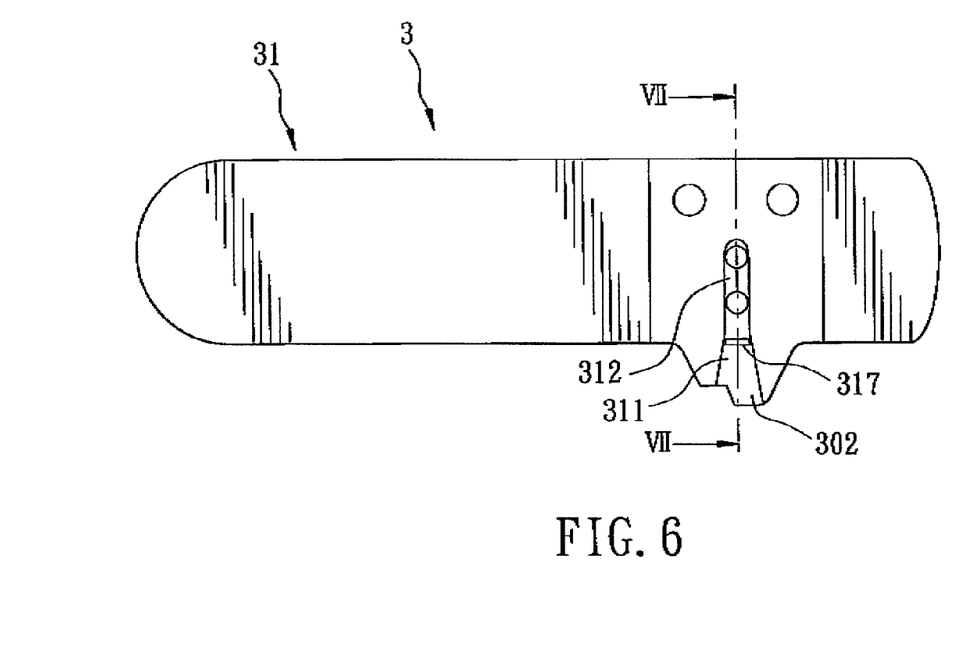
FIG. 6 is a top plan view illustrating still another preferred embodiment of the present invention.
Figure 7:
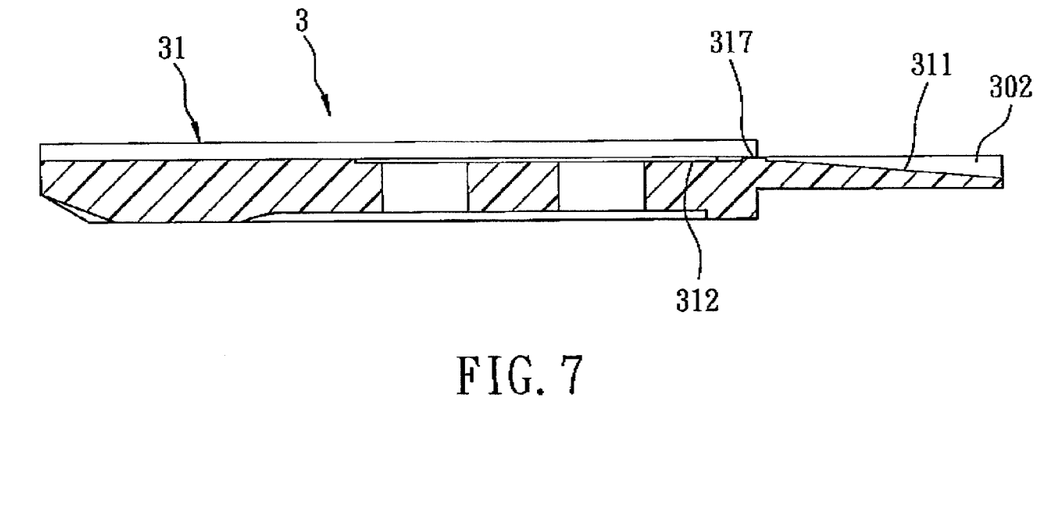
FIG. 7 is a sectional view taken along line VII-VII in FIG. 6.

Referring to FIG. 6, in another preferred embodiment of the invention, the upstream recessed region 311 of the electrode support 31 is tapered from the opening 302 to the downstream recessed region 312. However, the downstream recessed region 312 has a shape substantially corresponding to a finger, and the width thereof is constant. The electrode support 31 further includes a stop rib 317 formed between the upstream recessed region 311 and the downstream recessed region 312. As shown in FIG. 7, the upstream recessed region 311 has an ascending inclined surface extending from the opening 302 to the stop rib 317. When a reaction reagent is applied to the downstream recessed region 312 to form the reaction reagent layer 5, the stop rib 317 may be used to prevent the reaction reagent from flowing to the opening 302.

Figure 8:
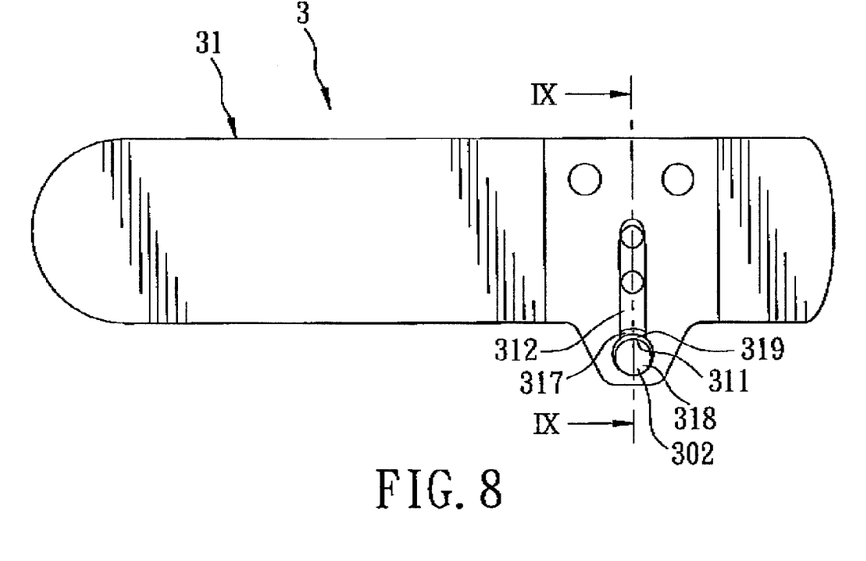
FIG. 8 is a top plan view illustrating still another preferred embodiment of the present invention.
Figure 9:
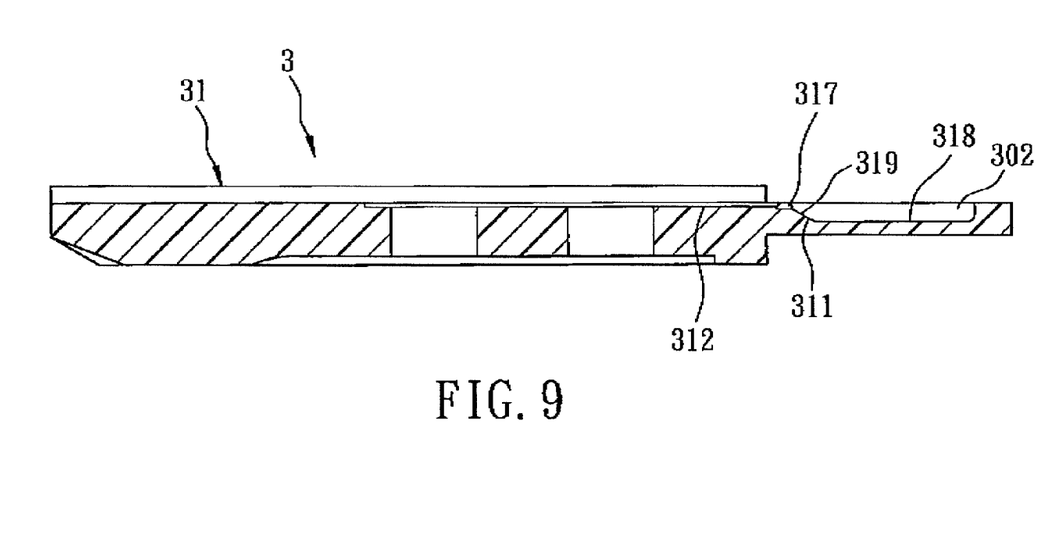
FIG. 9 is a sectional view taken along line IX-IX in FIG. 8.

Referring to FIGS. 8 and 9, in still another embodiment of the invention, the upstream recessed region 311 of the electrode support 31 has a circular shape, and the downstream recessed region 312 has the shape of a finger with a constant width. A stop rib 317 is disposed between the upstream recessed region 311 and the downstream recessed region 312. The upstream recessed region 311 has a groove bottom 318 and a groove wall 319 extending upward from the groove bottom 318. The groove wall 319 and the stop rib 317 cooperatively define an ascending inclined surface extending upward from the groove bottom 318.

Figure 5:
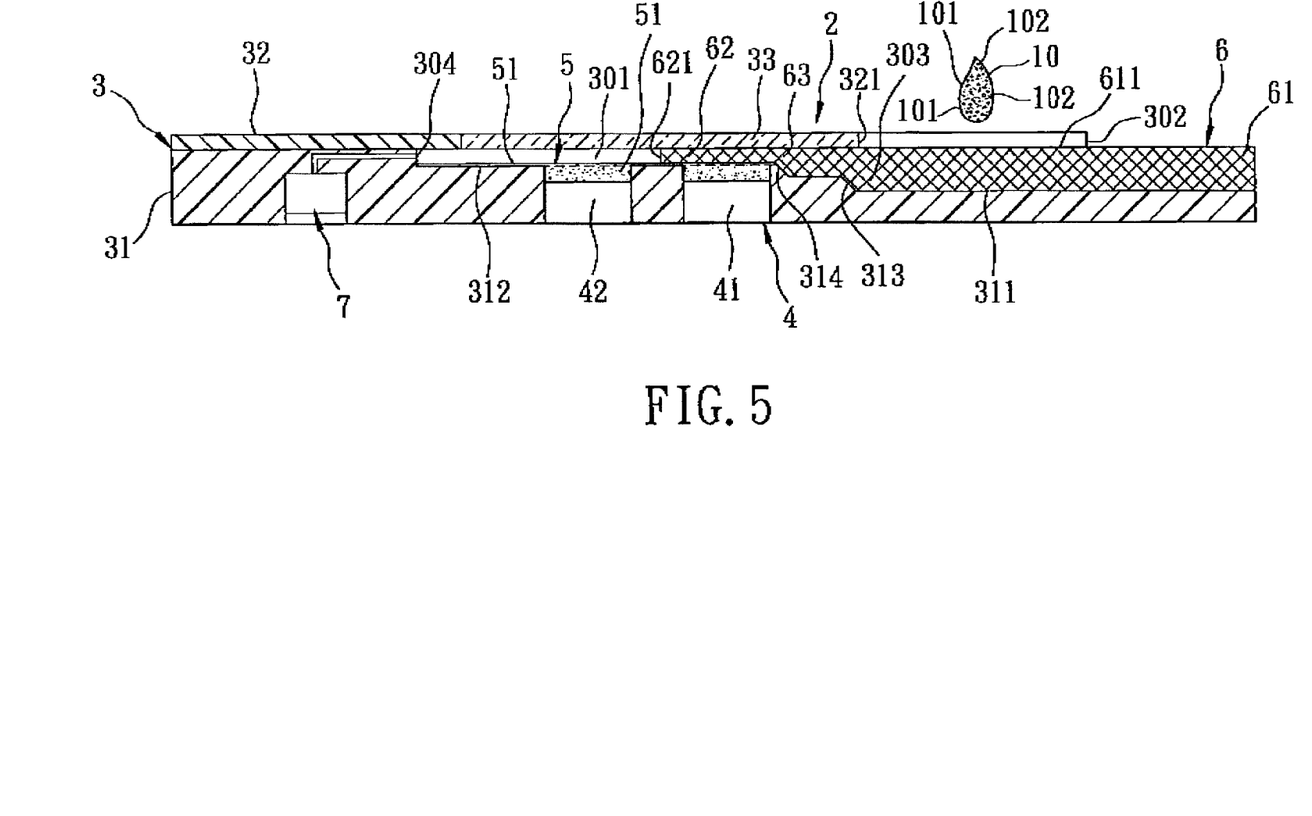
FIG. 5 is a sectional view showing another preferred embodiment of an electrochemical sensor strip according to the present invention.

Referring to FIG. 5, according to still another preferred embodiment of this invention, the electrochemical sensor 2 may further comprise a suction unit 7. The housing 3 further includes a suction port 304 communicated with the sample receiving space 301. The suction unit 7 is coupled to the housing 3 and communicated with the suction port 304 for sucking the fluid 10 into the sample receiving space 301. In order to avoid attenuation of suction forces, the vent holes 323 shown in FIG. 4 are not provided in the cover plate 32 shown in FIG. 5. The suction port 304 is formed in the electrode support 31. The suction unit 7 may be a micropump.

According to the present invention, because the sample access region 611 of the filter 6 is spaced apart from the electrode unit 4 in a direction substantially along the plane of the electrode support 31 to permit the fluid 10 to flow laterally to the electrode unit 4, only the filter 6 is needed to separate the target analyte from the interfering matter. Therefore, multiple filter layers used in the electrochemical sensor disclosed in U.S. Pat. No. 5,628,890 are not required in the present invention. In addition, because the filter 6 extends into the sample receiving space 301, the time needed by the target analyte to flow to the reaction reagent layer 5 and to the electrode unit 4 is reduced, and the result of detection can be obtained at a relatively fast rate.

Due to the tapering configuration, the volume and area of the filter 6 can be relatively reduced so that the amount of the fluid needed for analysis may be reduced. The tapering configuration also permits the fluid to easily gather at the tip end of the filter 6 and flow to the reaction reagent layer 5.

Because the filter 6 extends over a portion of the reaction reagent layer 5 and above at least one of the electrodes 41, 42, the distance that the fluid 10 must travel to the reaction reagent layer 5 and the electrode unit 4 decreases, and the time needed by the fluid 10 to travel is reduced. When the fluid 10 passes through the stepped portions 313, 314, the interfering matter can be retarded from flowing forward due to gravity.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An electrochemical sensor strip comprising:
    a housing including an electrode support and a cover plate, which cooperatively define a sample receiving space, an opening, and a sample passage connected to said opening and said sample receiving space, said electrode support having an inner surface confronting said cover plate, an outer surface opposite to said inner surface, an upstream recessed region formed in said inner surface to define said sample passage, and a downstream recessed region formed in said inner surface to define said sample receiving space, and a plurality of through holes extending through said inner and outer surfaces within said downstream recessed region;
    a plurality of electrodes disposed respectively in said through holes, at least one of said electrodes having a lowered top surface that is lowered relative to said inner surface to define a shallow space within a respective one of said through hole;
    a reaction reagent layer disposed in said sample receiving space in contact with said electrodes and extending into said shallow space; and
    a filter that is made of a material having a porous structure and that extends into said sample receiving space from said opening and through said sample passage, said filter covering a portion of said reaction reagent layer and extending above said shallow space and said lower top surface;
    wherein said filter has a wide section disposed at said opening, and a narrow section disposed in said sample receiving space; and
    wherein said cover plate has a peripheral edge proximate to said opening, said wide section of said filter having a sample access region extending beyond said peripheral edge and exposed from said opening.

2. The electrochemical sensor strip of claim 1, wherein said electrode support includes a pair of said through holes, said electrodes including a first electrode and a working electrode disposed respectively in said through holes, said first electrode being one of a counter electrode, a reference electrode and a combination thereof.

3. The electrochemical sensor strip of claim 2, wherein said first electrode has said lowered top surface.

4. The electrochemical sensor strip of claim 2, wherein each of said first and working electrodes has said lower top surface, said filter extending above said lower top surface of one of said first and working electrodes.

5. The electrochemical sensor strip of claim 1, wherein said filter has a wide section disposed at said opening, and a narrow section disposed in said sample receiving space.

6. The electrochemical sensor strip of claim 5, wherein said filter further has a middle section interconnecting said wide and narrow sections and tapering gradually from said wide section to said narrow section.

7. The electrochemical sensor strip of claim 6, wherein said filter has a substantially triangular shape, said narrow section terminating at a tip end.

8. The electrochemical sensor strip of claim 7, wherein said tip end of said narrow section is rounded and has an arcuated profile.

9. The electrochemical sensor strip of claim 5, wherein said upstream recessed region is tapered from said opening to said downstream recessed region to receive said filter.

10. The electrochemical sensor strip of claim 5, wherein said upstream recessed region has a stepped surface that ascends from said opening to said downstream recessed region, and said filter extends along said stepped surface and is clamped between said electrode support and said cover plate.

11. The electrochemical sensor strip of claim 1, wherein said cover plate has a vent hole communicated with said sample receiving space.

12. The electrochemical sensor strip of claim 1, wherein said porous structure of said filter has a pore size in a range of 0.8 μm-8 μm.

13. The electrochemical sensor strip of claim 1, wherein said peripheral edge of said cover plate has a notch that is indented in a direction toward said sample receiving space, said sample access region of said wide section being exposed from said notch.

14. The electrochemical sensor strip of claim 1, wherein a gap between said upstream recessed region and said cover plate is gradually reduced in size in a direction from said opening to said sample receiving space so that said filter is subjected to a squeezing pressure, which increases from said opening to said sample receiving space.

15. The electrochemical sensor strip of claim 14, wherein said filter has a density that increases from said opening to said sample receiving space.

16. The electrochemical sensor strip of claim 14, wherein said porous structure of said filter has a pore size that decreases from said opening to said sample receiving space.

17. The electrochemical sensor strip of claim 1, further comprising a suction unit, said housing further including a suction port communicated with said sample receiving space, said suction unit being coupled to said housing and communicated with said suction port.

* * * * *